US010619221B2

(12) United States Patent
Cheong et al.

(10) Patent No.: US 10,619,221 B2
(45) Date of Patent: Apr. 14, 2020

(54) BIOMARKER FOR DETECTING HIGHLY PATHOGENIC VIRAL HEMORRHAGIC SEPTICEMIA VIRUS AND DIAGNOSTIC METHOD

(71) Applicant: REPUBLIC OF KOREA (NATIONAL FISHERIES RESEARCH AND DEVELOPMENT INSTITUTE), Busan (KR)

(72) Inventors: Jae Hun Cheong, Busan (KR); Hyun Kook Cho, Busan (KR); Mi So Seong, Busan (KR); Mi Young Cho, Busan (KR); Myoung Ae Park, Busan (KR); Bo-Young Jee, Busan (KR); Seong Don Hwang, Busan (KR); Jee Youn Hwang, Busan (KR)

(73) Assignee: REPUBLIC OF KOREA (NATIONAL FISHERIES RESEARCH AND DEVELOPMENT INSTITUTE), Busan (KR)

( * ) Notice: Subject to any disclaimer, the term of this patent is extended or adjusted under 35 U.S.C. 154(b) by 24 days.

(21) Appl. No.: 15/759,831

(22) PCT Filed: Apr. 12, 2017

(86) PCT No.: PCT/KR2017/003975
§ 371 (c)(1),
(2) Date: Mar. 14, 2018

(87) PCT Pub. No.: WO2017/188631
PCT Pub. Date: Nov. 2, 2017

(65) Prior Publication Data
US 2018/0251861 A1 Sep. 6, 2018

(30) Foreign Application Priority Data
Apr. 27, 2016 (KR) .................. 10-2016-0051750

(51) Int. Cl.
*C12Q 1/70* (2006.01)
*G01N 21/00* (2006.01)
*G01N 33/569* (2006.01)

(52) U.S. Cl.
CPC ............ *C12Q 1/701* (2013.01); *G01N 21/00* (2013.01); *G01N 33/56983* (2013.01); *G01N 2333/08* (2013.01)

(58) Field of Classification Search
None
See application file for complete search history.

(56) References Cited

U.S. PATENT DOCUMENTS

2009/0181363 A1* 7/2009 Dhar ...................... C12Q 1/686
435/5

FOREIGN PATENT DOCUMENTS

KR 10-1677012 B1 11/2016

OTHER PUBLICATIONS

International Search Report for PCT/KR2017/003975 dated Aug. 1, 2017 from Korean Intellectual Property Office.
NCBI, GenBank accession No. AE052923.1 (Sep. 21, 2011).
NCBI, GenBank accession No. JF792424.1 (Sep. 21, 2011).
Pierce et al., "Accurate Detection and Quantification of the Fish Viral Hemorrhagic Septicemia virus (VHSv) with a Two-Color Fluorometric Real-Time PCR Assay", Plos One. vol. 8, No. 8, document No. e71851, inner p. 1-12 (E-pub. Aug. 20, 2013).
Ito et al., "Virulence of viral haemorrhagic septicaemia virus (VHSV) genotype III in rainbow trout", Veterinary Research, vol. 47, No. 4, pp. 1-13 (E-pub. Jan. 8, 2016).
Einer-Jensen et al., "High virulence differences among phylogenetically distinct isolates of the fish rhabdovirus viral hemorrhagic septicaemia virus are not explained by variability of the surface glycoprotein G or the nonvirion protein Nv", Journal of General Virology (2014), 95, 307-316.

* cited by examiner

*Primary Examiner* — Stacy B Chen
(74) *Attorney, Agent, or Firm* — Revolution IP, PLLC

(57) ABSTRACT

A biomarker composition includes, as an active ingredient, one or at least two polypeptides having 5 to 120 consecutive amino acids that are selected from the group consisting of an amino acid in which serine (S) at the $56^{th}$ position is substituted with leucine (L), an amino acid in which serine (S) at the $8^{th}$ position is substituted with asparagines (N), an amino acid in which threonine (T) at the $81^{st}$ position is substituted with alanine (A), an amino acid in which valine (V) at the $88^{th}$ position is substituted with alanine (A), an amino acid in which glycine (G) at the $117^{th}$ position is substituted with asparatic acid (D), and an amino acid in which glutamic acid (E) at the $119^{th}$ position is substituted with lysine (K), within an amino acid sequence of VHSV represented by SEQ ID NO: 1.

2 Claims, 5 Drawing Sheets
Specification includes a Sequence Listing.

[FIGURE 1]
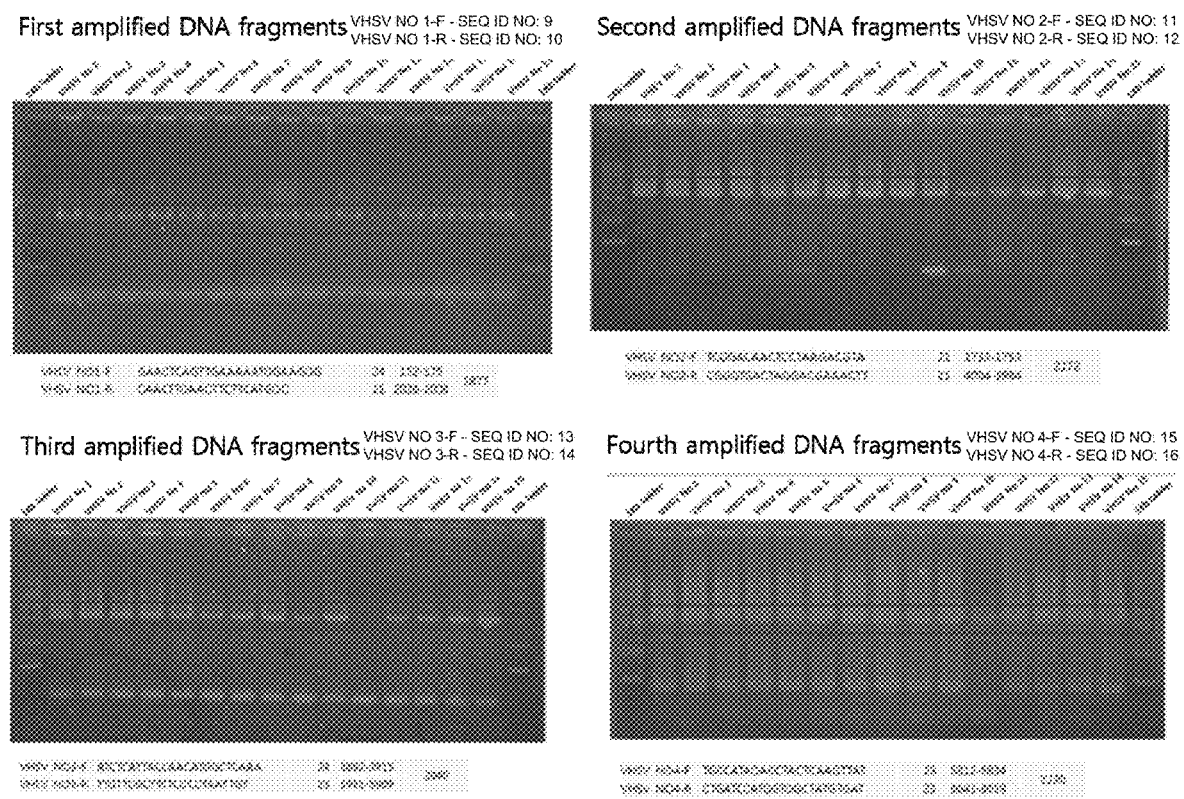

[FIGURE 2]
Comments for pcDNA3:
  5446 nucleotides
CMV promoter: bases 209-863
T7 promoter: bases 864-882
Polylinker: bases 889-994
Sp6 promoter: bases 999-1016
BGH poly A: bases 1018-1249
SV40 promoter: bases 1790-2115
SV40 origin of replication: bases 1984-2069
Neomycin ORF: bases 2151-2945
SV40 poly A: bases 3000-3372
ColE1 origin: bases 3632-4305
Ampicillin ORF: bases 4450-5310
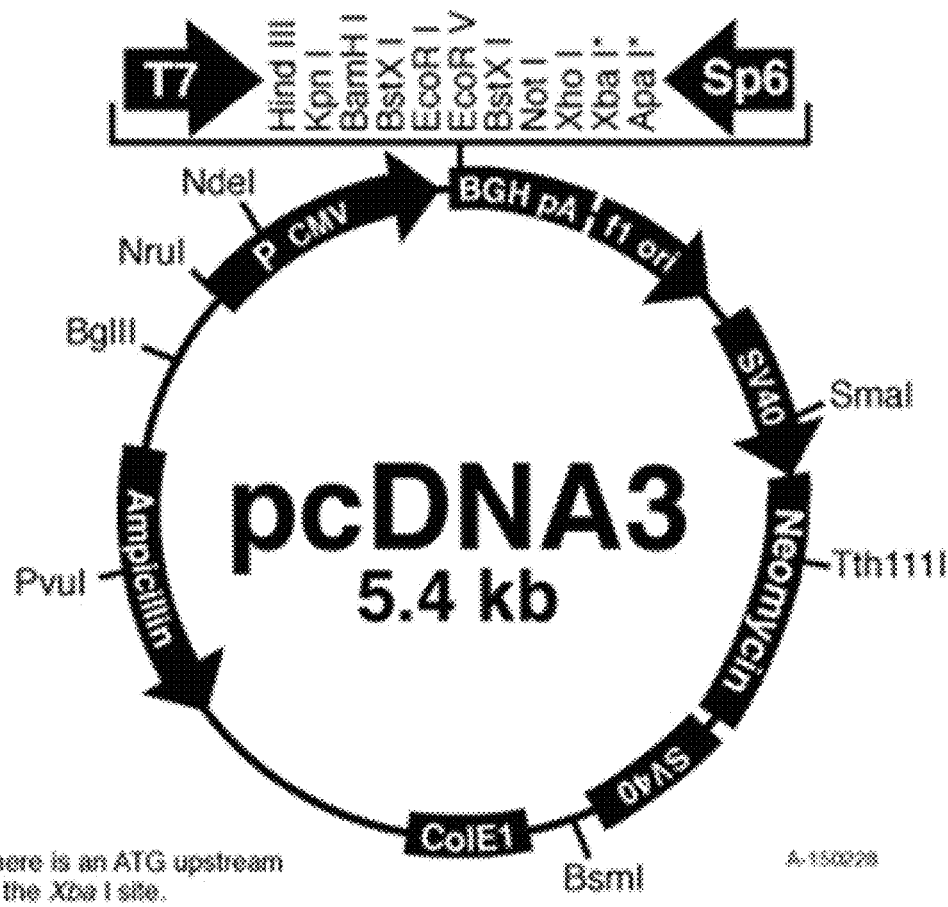

[FIGURE 6]
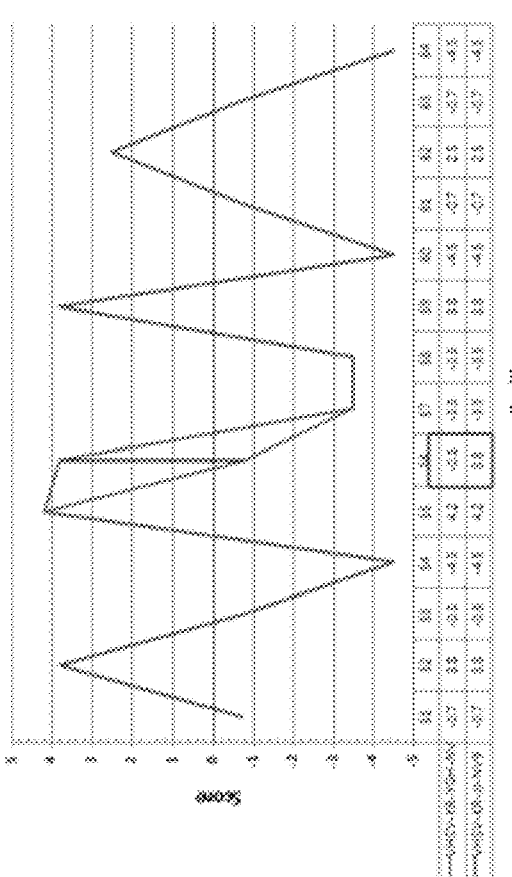
A
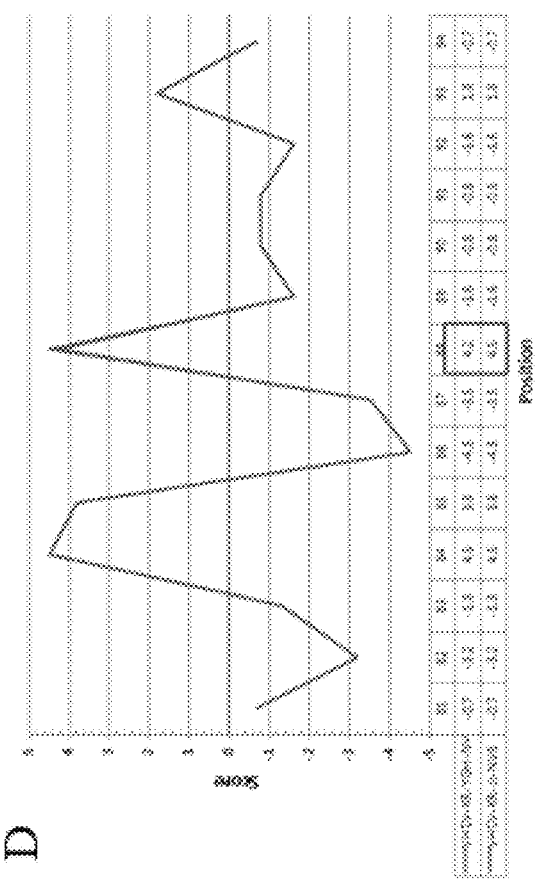
B
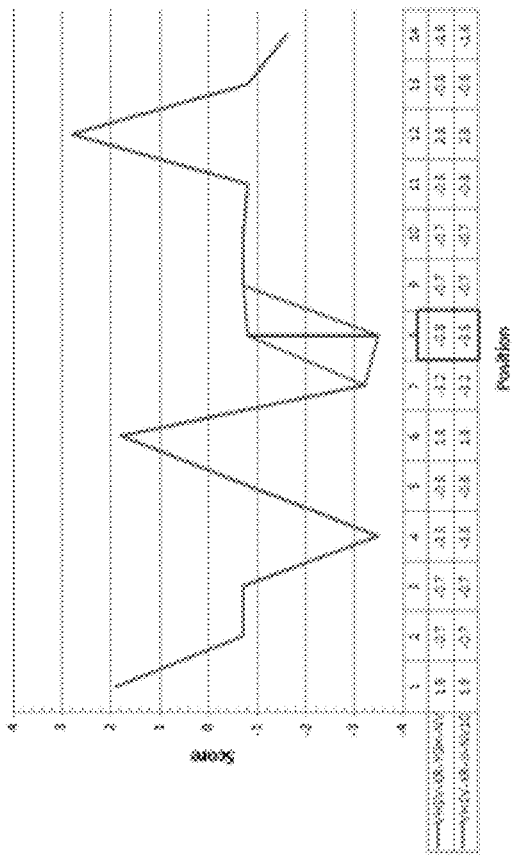
C
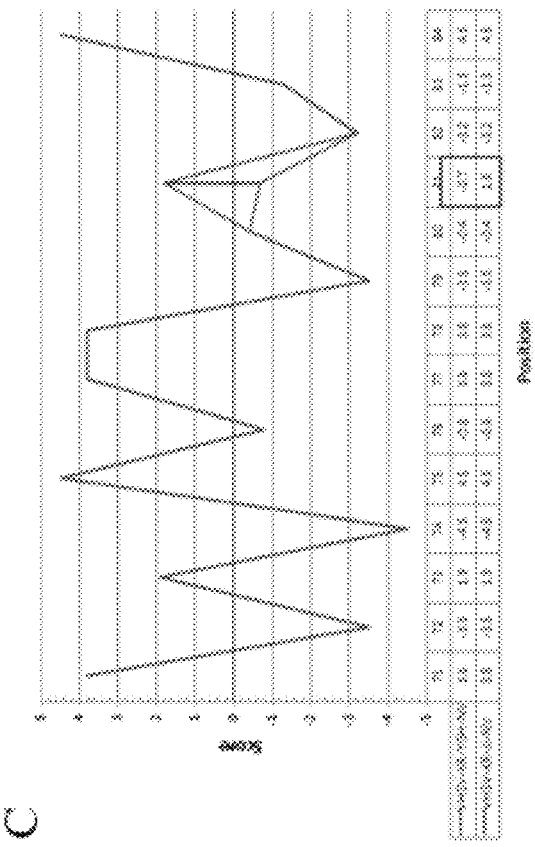
D

SEQUENCE LISTING

<160> NUMBER OF SEQ ID NOS: 16

<210> SEQ ID NO 1
<211> LENGTH: 122
<212> TYPE: PRT
<213> ORGANISM: Viral hemorrhagic septicemia virus

<400> SEQUENCE: 1

Met Thr Thr Gln Ser Ala His Ser Thr Thr Ser Phe Ser Pro Leu Val
1               5                   10                  15

Leu Arg Glu Met Ile Glu Tyr Arg Leu Thr Phe Asp Pro Ser Asn Tyr
            20                  25                  30

Leu Asn Ser Asp Leu Asp Arg Ser Glu Ile Ser Ala Thr Asp Phe Phe
        35                  40                  45

Glu Thr Thr Leu Ser Arg Val Ser Glu Asp Leu Arg Thr Cys Thr Arg
        50              55                  60

Leu Pro Tyr Leu His Val Leu Asp Met Arg Ile Ser Leu Leu Glu Gly
65                  70                  75                  80

Thr His Tyr Ile Leu Arg Asn Val Pro Ser Ser Pro Ala Thr Thr Gly
                85                  90                  95

Arg Pro Ser Asp Pro Gly Leu Phe Ile Ile Ser Leu Glu Gly Met Lys
            100                 105                 110

Thr Leu Thr Asn Gly Ser Glu Ser Pro Pro
        115                 120

<210> SEQ ID NO 2
<211> LENGTH: 369
<212> TYPE: DNA
<213> ORGANISM: Viral hemorrhagic septicemia virus

<400> SEQUENCE: 2
atgacgaccc agtcggcaca cagcacaacc agcttctctc cacttgtcct tcgcgagatg      60
atcgagtaca gactaacatt tgacccaagc aactacctca acagtgacct cgatcggtca     120
gaaatctccg ctacagactt cttcgagaca actcttttcta gagtctcaga ggatctaagg    180
acctgcacac gacttcccta cctccatgtg cttgacatga ggataagtct cctagaggga    240
actcattaca tactaaggaa tgtccccctcc agtcctgcta caactggtag accatctgat    300
cctggactct tcatcatttc acttgaggga atgaagacct tgacgaatgg ctccgaatct    360
cccccatga                                                             369

<210> SEQ ID NO 3
<211> LENGTH: 20
<212> TYPE: DNA
<213> ORGANISM: Viral hemorrhagic septicemia virus

<400> SEQUENCE: 3
cggcacacaa cacaaccagc                                                  20

<210> SEQ ID NO 4
<211> LENGTH: 25
<212> TYPE: DNA
<213> ORGANISM: Viral hemorrhagic septicemia virus

<400> SEQUENCE: 4
ctagagtctt agaggatcta aggac                                            25

<210> SEQ ID NO 5
<211> LENGTH: 23
<212> TYPE: DNA
<213> ORGANISM: Viral hemorrhagic septicemia virus

<400> SEQUENCE: 5
gtctcctaga gggagctcat tac                                              23

<210> SEQ ID NO 6
<211> LENGTH: 23
<212> TYPE: DNA
<213> ORGANISM: Viral hemorrhagic septicemia virus

<400> SEQUENCE: 6
ctaaggaata tcccctccag tcc                                              23

-continued

```
<210> SEQ ID NO 7
<211> LENGTH: 22
<212> TYPE: DNA
<213> ORGANISM: Viral hemorrhagic septicemia virus

<400> SEQUENCE: 7
gacgaatgac tccgaatctc cc                                               22

<210> SEQ ID NO 8
<211> LENGTH: 22
<212> TYPE: DNA
<213> ORGANISM: Viral hemorrhagic septicemia virus

<400> SEQUENCE: 8
gacgaatggc tccaaatctc cc                                               22

<210> SEQ ID NO 9
<211> LENGTH: 24
<212> TYPE: DNA
<213> ORGANISM: Artificial Sequence
<220> FEATURE:
<223> OTHER INFORMATION: Primer (VHSV NO 1-F)

<400> SEQUENCE: 9
gaactcagtt gaaaaatgga aggg                                             24

<210> SEQ ID NO 10
<211> LENGTH: 21
<212> TYPE: DNA
<213> ORGANISM: Artificial Sequence
<220> FEATURE:
<223> OTHER INFORMATION: Primer (VHSV NO 1-R)

<400> SEQUENCE: 10
caacttgaac ttcttcatgg c                                                21

<210> SEQ ID NO 11
<211> LENGTH: 21
<212> TYPE: DNA
<213> ORGANISM: Artificial Sequence
<220> FEATURE:
<223> OTHER INFORMATION: Primer (VHSV NO 2-F)

<400> SEQUENCE: 11
tcggacaact cctaagacgt a                                                21

<210> SEQ ID NO 12
<211> LENGTH: 21
<212> TYPE: DNA
<213> ORGANISM: Artificial Sequence
<220> FEATURE:
<223> OTHER INFORMATION: Primer (VHSV NO 2-R)

<400> SEQUENCE: 12
cgggtgacta ggacgaaact t                                                21

<210> SEQ ID NO 13
<211> LENGTH: 24
<212> TYPE: DNA
<213> ORGANISM: Artificial Sequence
<220> FEATURE:
<223> OTHER INFORMATION: Primer (VHSV NO 3-F)

<400> SEQUENCE: 13
atctcattac caacatggct caaa                                             24
```

```
<210> SEQ ID NO 14
<211> LENGTH: 23
<212> TYPE: DNA
<213> ORGANISM: Artificial Sequence
<220> FEATURE:
<223> OTHER INFORMATION: Primer (VHSV NO 3-R)

<400> SEQUENCE: 14
ttgttcgctt ctcccctaat tgt                                              23

<210> SEQ ID NO 15
<211> LENGTH: 23
<212> TYPE: DNA
<213> ORGANISM: Artificial Sequence
<220> FEATURE:
<223> OTHER INFORMATION: Primer (VHSV NO 4-F)

<400> SEQUENCE: 15
tgccatagac ctactcaagt tat                                              23

<210> SEQ ID NO 16
<211> LENGTH: 23
<212> TYPE: DNA
<213> ORGANISM: Artificial Sequence
<220> FEATURE:
<223> OTHER INFORMATION: Primer (VHSV NO 4-R)

<400> SEQUENCE: 16
ctgatccatg gtggctatgt gat                                              23
```

BIOMARKER FOR DETECTING HIGHLY PATHOGENIC VIRAL HEMORRHAGIC SEPTICEMIA VIRUS AND DIAGNOSTIC METHOD

TECHNICAL FIELD

The present invention relates to a biomarker composition for detecting a highly pathogenic viral hemorrhagic septicemia virus (VHSV) and a method of diagnosing VHSV infection.

BACKGROUND ART

Viral hemorrhagic septicemia virus (VHSV) is a viral pathogen that causes severe loss of many cultured fish including flatfish, and is regarded as a cause of viral hemorrhagic septicemia (VHS).

VHS was first reported as a critical viral disease of the rainbow trout. However, it has been recently reported that VHS occurs in various fish, including not only salmonidae fish, such as trout, rainbow trout, coho salmon, brook trout, brown trout, or steelhead trout, but also fish in natural water system, such as cod or herring, and cultured marine fish, such as flatfish, and that VHS occurs predominantly in Europe, North America, and Asia.

In South Korea, VHS has been consistently reported in Gyeongbuk and Jeju areas since it was first reported in flatfish in 2001. In particular, VHS causes mortality not only in small fish, but also large fish from late autumn to spring seasons, when the water temperature falls below 14° C. When examining the infected flatfish with the naked eyes, body color darkening, systemic bleeding, abdominal distension and hernia by abdominal reservoir, gill fading, red spot-like hemorrhage on a blind side, or the like are observed.

VHSV is a negative single-stranded RNA virus, which was first reported at the Symposium on Fish Pathology held by the World Organization for Animal Health in 1963. VHSV is bullet-shaped, approximately 180 nm in length and 60 nm in diameter, and has a size of 11 kb. VHSV belongs to the family Rhabdovirus containing six genes, nucleocapsid protein (N), polymerase-associated phosphoprotein (P), matrix protein (M), surface glycoprotein (G), a unique non-virion protein (NV), and virus polymerase (L), and among the six proteins producing the VHSV, the NV protein has been reported to be associated with the pathogenicity of the VHSV.

The VHSV is genetically mutated at a very high rate, and thus, new variant VHS viruses are constantly on the rise.

However, as a result of analyzing total gene sequence information of low pathogenic VHSV and highly pathogenic VHSV that are obtained in South Korea, there was no difference in NV gene sequences that have been reported to be related to the pathogenicity of the VHSV. In this regard, research on the early detection method of new VHSV with high pathogenic is essential for the protection of flatfish and various fishes at home and abroad.

DETAILED DESCRIPTION OF THE INVENTION

Technical Problem

The present invention provides a biomarker composition for detecting a highly pathogenic viral hemorrhagic septicemia virus (VHSV) for the early detection of a new VHSV with high pathogenicity, and accordingly provides a method of diagnosing VHSV infection.

Technical Solution

The present invention provides a biomarker composition for detecting viral hemorrhagic septicemia virus (VHSV), the biomarker including, as an active ingredient, one or at least two polypeptides having 5 to 120 consecutive amino acids, wherein the one or at least two polypeptides are selected from the group consisting of an amino acid in which serine (S) at the $56^{th}$ position is substituted with leucine (L), an amino acid in which serine (S) at the $8^{th}$ position is substituted with asparagines (N), an amino acid in which threonine (T) at the $81^{st}$ position is substituted with alanine (A), an amino acid in which valine (V) at the $88^{th}$ position is substituted with alanine (A), an amino acid in which glycine (G) at the $117^{th}$ position is substituted with asparatic acid (D), and an amino acid in which glutamic acid (E) at the $119^{th}$ position is substituted with lysine (K), within an amino acid sequence of NV protein of VHSV represented by SEQ ID NO: 1.

The present invention provides a biomarker composition for detecting viral hemorrhagic septicemia virus (VHSV), the biomarker composition including, as an active ingredient, one or at least two polynucleotides having 5 to 360 consecutive nucleotides, wherein the one or at least two polynucleotides are selected from the group consisting of a gene in which a base at the $23^{rd}$ position is substituted with adenosine (A), a gene in which a base at the $167^{th}$ position is substituted with thymine (T), a gene in which a base at the $241^{st}$ position is substituted with guanine (G), a gene in which a base at the $262^{nd}$ position is substituted with adenosine (A), a gene in which a base at the $350^{th}$ position is substituted with adenosine (A), and a gene in which a base at the $355^{th}$ position is substituted with adenosine (A), within a NV gene of VHSV consisting of a nucleotide sequence represented by SEQ ID NO: 2.

The present invention provides a method of providing information for diagnosis of viral hemorrhagic septicemia virus (VHSV), the method including: sequencing DNA sequences of NV gene of VHSV from a VHSV-infected subject to obtain DNA sequence information; converting the DNA sequence information obtained from the sequencing into amino acid information; and detecting one or at least two amino acids selected from the group consisting of an amino acid in which serine (S) at the $56^{th}$ position is substituted with leucine (L), an amino acid in which serine (S) at the $8^{th}$ position is substituted with asparagines (N), an amino acid in which threonine (T) at the $81^{st}$ position is substituted with alanine (A), an amino acid in which valine (V) at the $88^{th}$ position is substituted with alanine (A), an amino acid in which glycine (G) at the $117^{th}$ position is substituted with asparatic acid (D), and an amino acid in which glutamic acid (E) at the $119^{th}$ position is substituted with lysine (K).

The present invention provides a kit for detecting viral hemorrhagic septicemia virus (VHSV), the kit including an agent detecting one or at least two amino acids selected from the group consisting of an amino acid in which serine (S) at the $56^{th}$ position is substituted with leucine (L), an amino acid in which serine (S) at the $8^{th}$ position is substituted with asparagines (N), an amino acid in which threonine (T) at the $81^{st}$ position is substituted with alanine (A), an amino acid in which valine (V) at the $88^{th}$ position is substituted with alanine (A), an amino acid in which glycine (G) at the $117^{th}$ position is substituted with asparatic acid (D), and an amino acid in which glutamic acid (E) at the $119^{th}$ position is substituted with lysine (K), within an amino acid sequence of NV protein of VHSV represented by SEQ ID NO: 1.

In addition, the present invention provides a kit for detecting viral hemorrhagic septicemia virus (VHSV), the kit including an agent detecting one or at least two polynucleotides selected from the group consisting of a gene in which a base at the 23$^{rd}$ position is substituted with adenosine (A), a gene in which a base at the 167$^{th}$ position is substituted with thymine (T), a gene in which a base at the 241$^{st}$ position is substituted with guanine (G), a gene in which a base at the 262$^{nd}$ position is substituted with adenosine (A), a gene in which a base at the 350$^{th}$ position is substituted with adenosine (A), and a gene in which a base at the 355$^{th}$ position is substituted with adenosine (A), within a NV gene of VHSV gene consisting of a nucleotide sequence represented by SEQ ID NO: 2.

Advantageous Effects of the Invention

According to the present invention, mutations in six amino acids are confirmed in a unique non-virion (NV) protein that is related to high pathogenicity of viral hemorrhagic septicemia virus (VHSV). In particular, among the six amino acid mutants, high pathogenicity was induced when an amino acid, specifically serine at the 56$^{th}$ position, was substituted with leucine. Therefore, the six amino acid mutants can be used as a biomarker to detect new VHSV, and can be further utilized as a diagnostic biomarker for VHS to diagnose infection of fish VHSV in an early stage.

DESCRIPTION OF THE DRAWINGS

FIG. 1 shows the results confirming amplified DNA fragments obtained after PCR is performed for complete decoding of viral hemorrhagic septicemia virus (VHSV).

FIG. 2 shows the results confirming a mutated portion of an amino acid sequence of a unique non-virion (NV) protein upon conversion of the amplified DNA sequences of the NV protein region of VHSV into amino acid sequences.

FIG. 3 is a schematic diagram of pcDNA3 vector used for cloning to efficiently express NV mutant genes of VHSV in a cell into a protein.

FIG. 4 shows the results confirming ATP levels according to the expression of the NV protein of wild-type VHSV in a cell after performing transduction on a flatfish cell with a vector including the cloned NV gene of the wild-type VHSV.

FIG. 5 shows the results confirming ATP levels obtained after performing transduction on a flatfish cell with a vector manufactured to express each of the six amino acid mutants and inducing expression of the flatfish cell, to thereby determine pathogenicity of six NV amino acid mutants of VHSV.

FIG. 6 shows results confirming hydropathy index of the NV mutant proteins of VHSV, and more specifically, FIG. 6A shows a result confirming a change in ATP levels in a mutant in which serine at the 8$^{th}$ position is substituted with asparagine, FIG. 6B shows a result confirming a change in ATP levels in a mutant in which serine at the 56$^{th}$ position is substituted with leucine, FIG. 6C shows a result confirming a change in ATP levels in a mutant in which threonine at the 81$^{st}$ position is substituted with alanine, and FIG. 6D shows a result confirming a change in ATP levels in a mutant in which valine (V) at the 88$^{th}$ position is substituted with alanine (A).

BEST MODE

The present invention provides a biomarker composition for detecting viral hemorrhagic septicemia virus (VHSV), the biomarker including, as an active ingredient, one or at least two polypeptides having 5 to 120 consecutive amino acids, wherein the one or at least two polypeptides are selected from the group consisting of an amino acid in which serine (S) at the 56$^{th}$ position is substituted with leucine (L), an amino acid in which serine (S) at the 8$^{th}$ position is substituted with asparagines (N), an amino acid in which threonine (T) at the 81$^{st}$ position is substituted with alanine (A), an amino acid in which valine (V) at the 88$^{th}$ position is substituted with alanine (A), an amino acid in which glycine (G) at the 117$^{th}$ position is substituted with asparatic acid (D), and an amino acid in which glutamic acid (E) at the 119$^{th}$ position is substituted with lysine (K), within an amino acid sequence of amino acid sequence of NV protein of VHSV represented by SEQ ID NO: 1.

The amino acid sequence of VHSV represented by SEQ ID NO: 1 may be include a structural protein of VHSV, called a unique non-virion (NV) protein region.

Figure 3:
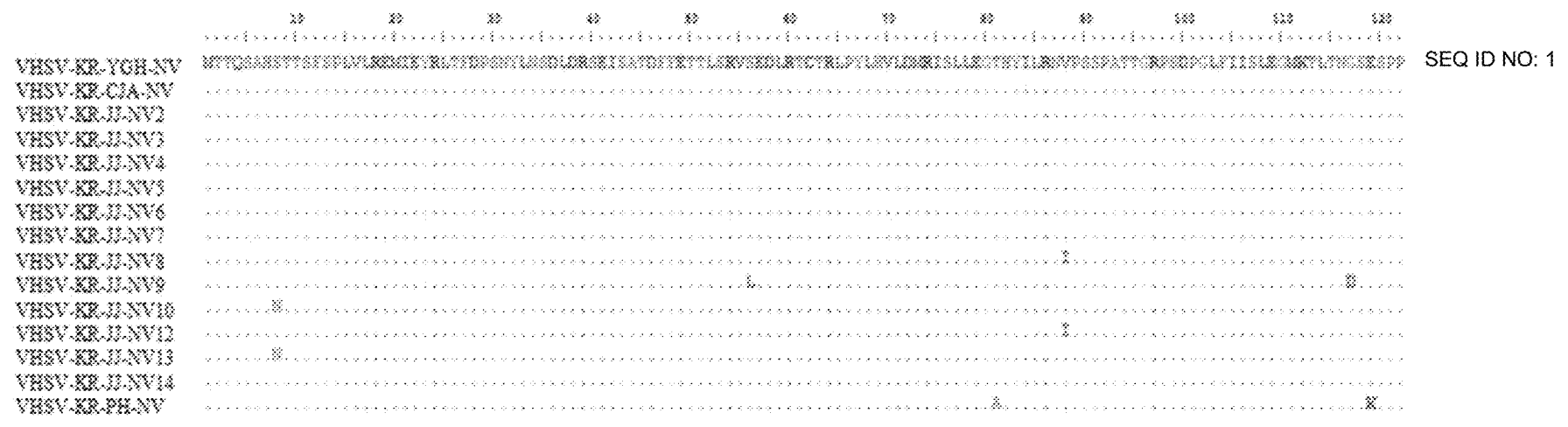

In an embodiment of the present invention, as shown in FIG. 3, mutations in six amino acids are confirmed in the NV protein that is related to high pathogenicity of VHSV. In particular, induction of high pathogenicity is also confirmed when an amino acid, specifically serine at the 56$^{th}$ position, is substituted with leucine, among the six amino acid mutants. Therefore, the six amino acid mutants can be used as a biomarker to detect new VHSV, and can be further utilized as a diagnostic biomarker for VHS to diagnose infection of fish VHSV in an early stage.

The present invention provides a biomarker composition for detecting VHSV, the biomarker composition including, as an active ingredient, one or at least two polynucleotides having 5 to 360 consecutive nucleotides of NV protein, wherein the one or at least two polynucleotides are selected from the group consisting of a gene in which a base at the 23$^{rd}$ position is substituted with adenosine (A), a gene in which a base at the 167$^{th}$ position is substituted with thymine (T), a gene in which a base at the 241$^{st}$ position is substituted with guanine (G), a gene in which a base at the 262$^{nd}$ position is substituted with adenosine (A), a gene in which a base at the 350$^{th}$ position is substituted with adenosine (A), and a gene in which a base at the 355$^{th}$ position is substituted with adenosine (A), within a VHSV gene consisting of a nucleotide sequence represented by SEQ ID NO: 2.

The present invention provides a method of providing information for diagnosis of VHSV, the method including: sequencing DNA sequences of NV gene of VHSV from a VHSV-infected subject to obtain DNA sequence information; converting the DNA sequence information obtained from the sequencing into amino acid information; and detecting one or at least two amino acids selected from the group consisting of an amino acid in which serine (S) at the 56$^{th}$ position is substituted with leucine (L), an amino acid in which serine (S) at the 8$^{th}$ position is substituted with asparagines (N), an amino acid in which threonine (T) at the 81$^{st}$ position is substituted with alanine (A), an amino acid in which valine (V) at the 88$^{th}$ position is substituted with alanine (A), an amino acid in which glycine (G) at the 117$^{th}$ position is substituted with asparatic acid (D), and an amino acid in which glutamic acid (E) at the 119$^{th}$ position is substituted with lysine (K).

The subject may be selected from the group consisting of rockfish, flatfish, snapper, convict grouper, gray mullet, sea bass, gizzard shad, turbot, swellfish, mackerel, spotty belly greenling, tuna, croaker, yellow tail, horse mackerel, carp, leather carp, Japanese eel, catfish, loach, and crucian, and preferably, may be flatfish, but is not limited thereto.

Sequence analysis in the sequencing step may be performed by using all methods known in the art. Specifically, although not limited thereto, an automated sequencer may be used, or at least one method selected from known methods such as pyrosequencing, PCR-restriction fragment length polymorphism (RELP), PCR-single strand conformation polymorphism (SSCP), PCR-specific sequence oligonucleotide (SSO), allele-specific oligonucleotide (ASO) hybridization in combination with PCR-SSO and dot hybridization, TaqMan-PCR, MALDI-TOF/MS, rolling circle amplification (RCA), high resolution melting (HRM), primer elongation, southern blot hybridization, and dot hybridization.

The DNA sequence information obtained from the sequencing step may include a non-structural protein of VHSV, called an NV protein region.

The present invention provides a kit for detecting VHSV, the kit including an agent detecting one or at least two amino acids selected from the group consisting of an amino acid in which serine (S) at the $56^{th}$ position is substituted with leucine (L), an amino acid in which serine (S) at the $8^{th}$ position is substituted with asparagines (N), an amino acid in which threonine (T) at the $81^{st}$ position is substituted with alanine (A), an amino acid in which valine (V) at the $88^{th}$ position is substituted with alanine (A), an amino acid in which glycine (G) at the $117^{th}$ position is substituted with asparatic acid (D), and an amino acid in which glutamic acid (E) at the $119^{th}$ position is substituted with lysine (K), within an amino acid sequence of VHSV represented by SEQ ID NO: 1.

In addition, the present invention provides a kit for VHSV, the kit including an agent detecting one or at least two polynucleotides selected from the group consisting of a gene in which a base at the $23^{rd}$ position is substituted with adenosine (A), a gene in which a base at the $167^{th}$ position is substituted with thymine (T), a gene in which a base at the $241^{st}$ position is substituted with guanine (G), a gene in which a base at the $262^{nd}$ position is substituted with adenosine (A), a gene in which a base at the $350^{th}$ position is substituted with adenosine (A), and a gene in which a base at the $355^{th}$ position is substituted with adenosine (A), within a NV gene of VHSV consisting of a nucleotide sequence represented by SEQ ID NO: 2.

The kit for detecting VHSV according to the present invention may include not only a primer or an antibody that can selectively recognize a gene having a base substitution or a protein of the gene, but also a tool and a reagent typically used in the art for immunological analysis.

Examples of such a tool or a reagent include an appropriate carrier, a labeling material capable of generating a detectable signal, a solubilizer, a buffer, and a stabilizer, but are not limited thereto. When the labeling material is an enzyme, the labeling material may include a substrate that can measure the activity of the enzyme and a reaction terminator. The appropriate carrier may be, although not limited thereto, a soluble carrier, e.g., a physiologically acceptable buffer known in the art including PBS, or an insoluble carrier, e.g., polystyrene, polyethylene, polypropylene, polyester, polyacrylonitrile, fluoride resin, cross-linked dextran, polysaccharide, polymer such as magnetic fine particles coated metal on latex, other papers, glass, metal, agarose, and a combination thereof.

The kit for detecting VHSV according to the present invention may be preferably an RT-PCR kit, a DNA kit, or a protein chip kit.

The RT-PCR kit may include a pair of primers specific to a marker gene, and in addition, may include a test tube or other appropriate containers, a reaction buffer solution (having various pH and magnesium concentration), deoxynucleotides (dNTPs), Taq-polymerase, and an enzyme such as reverse transcriptase, DNAse, RNAse inhibitor DEPC-water, sterilized water, and the like.

The DNA chip kit may include a substrate on which cDNA or oligonucleotide, which corresponds to a gene or a fragment thereof, is attached, and a reagent for producing a fluorescent-labeled probe, an agent, an enzyme, or the like, wherein the substrate may include cDNA or oligonucleotide, which corresponds to a control gene or a fragment thereof.

The protein chip kit may be a kit including a substrate fixed at high density on which at least one antibody against a marker is arranged at a predetermined position. Regarding a method of using a protein chip, a protein is separated from a sample, the separated protein is hybridized with a protein chip to form an antigen-antibody complex, and then, the protein chip is decoded to determine the presence or expression level of the protein.

MODE OF THE INVENTION

Hereinafter, the present disclosure is described in detail with reference to Examples. However, Examples shown and described herein are illustrative examples of the present invention and are not intended to otherwise limit the scope of the inventive concept in any way; rather, these Examples are provided so that the present disclosure will be thorough and complete, and will fully convey the concept of the inventive concept to those skilled in the art.

<Example 1> Confirmation of Mutation in Whole Genes in Viral Hemorrhagic Septicemia Virus (VHSV)

For the early diagnosis of highly pathogenic VHSV causing severe deaths of various cultured fish including flatfish, the whole gene mutation sequences of 13 types of VHSV inducing fish death were obtained in Korean coastal areas, and then subjected to sequencing for 3 years from 2012 to 2014.

1. Separation of VHSV

To obtain VHSV from intestines of flatfish showing symptoms of VHS, intestinal tissues obtained from 13 flatfish were pulverized in an MEM medium containing antibiotics and fetal bovine serum, and then, the pulverized product was centrifuged at a speed of 13,000 rpm at a temperature of 4° C. for 10 minutes, followed by being filtered using a 0.45 μm membrane.

The resulting pulverized product obtained after the filtration was inoculated with EPC flatfish cells at a dilution ratio in a range of 1:100 to 1:1,000, and the cells were cultured at a temperature of 16° C. Then, through microscopic examination, the abnormality of the cells was confirmed.

When pathological phenomenon of the cells was clearly identified, the cell culture was collected, stored at a temperature of −80° C., and then, quantified by the standard plaque assay.

TABLE 1

| Name | Region | Year |
| --- | --- | --- |
| VHSV-KR-JJ-2 | Jeju | 2012 |
| VHSV-KR-JJ-3 | Jeju | 2012 |
| VHSV-KR-JJ-4 | Jeju | 2012 |
| VHSV-KR-JJ-5 | Jeju | 2012 |
| VHSV-KR-JJ-6 | Jeju | 2012 |
| VHSV-KR-JJ-7 | Jeju | 2013 |
| VHSV-KR-JJ-8 | Jeju | 2013 |
| VHSV-KR-JJ-9 | Jeju | 2013 |
| VHSV-KR-JJ-10 | Jeju | 2013 |
| VHSV-KR-JJ-12 | Jeju | 2014 |
| VHSV-KR-JJ-13 | Jeju | 2014 |
| VHSV-KR-JJ-14 | Jeju | 2014 |
| VHSV-KR-PH | Pohang | 2013 |

2. VHSV Genome Separation and Gene Sequencing

Based on the gene sequences of VHSV NV protein (SEQ ID NO: 2), DNA polymerase chain reaction (PCR) primers required for the sequencing of the whole virus genes were prepared as shown in Table 2.

TABLE 2

| Primer | Sequence | Position | Size |
|---|---|---|---|
| VHSV NO 1-F | GAACTCAGTTGAAAAATGGAAGGG (SEQ ID NO: 9) 24 bp | 152-175 | 1877 |
| VHSV NO 1-R | CAACTTGAACTTCTTCATGGC (SEQ ID NO: 10) 21 bp | 2028-2008 | |
| VHSV NO 2-F | TCGGACAACTCCTAAGACGTA (SEQ ID NO: 11) 21 bp | 1733-1753 | 2272 |
| VHSV NO 2-R | CGGGTGACTAGGACGAAACTT (SEQ ID NO: 12) 21 bp | 4004-3984 | |
| VHSV NO 3-F | ATCTCATTACCAACATGGCTCAAA (SEQ ID NO: 13) 24 bp | 3892-3915 | 2040 |
| VHSV NO 3-R | TTGTTCGCTTCTCCCCTAATTGT (SEQ ID NO: 14) 23 bp | 5931-5909 | |
| VHSV NO 4-F | TGCCATAGACCTACTCAAGTTAT (SEQ ID NO: 15) 23 bp | 5812-5834 | 2230 |
| VHSV NO 4-R | CTGATCCATGGTGGCTATGTGAT (SEQ ID NO: 16) 23 bp | 8041-8019 | |

1 µM of each primer, 2 mM of each dNTP, 10× Buffer, and 5 U of nTaq DNA polymerase (Enzynomics, Korea) were added to 100 ng of template pcDNA3-NV DNA, and distilled water was added thereto so that a final volume of the PCR mixture was 20 µL. The PCR conditions were 25 cycles of pre-denaturation at a temperature of 95° C. for 5 minutes, denaturation at a temperature of 95° C. for 30 seconds, annealing at a temperature of 58° C. for 30 seconds, and extension at a temperature of 72° C. for 30 seconds.

Afterwards, the PCR products were subjected to post-extension at a temperature of 72° C. for 5 minutes. The amplified PCR products were subjected to agarose gel electrophoresis using 1× buffer as a buffer solution required for electrophoresis, wherein agarose gel used herein was 1% agarose gel with ethidium bromide. DNA bands were observed using an UV detector.

The amplified PCR products were recovered by using the gel purification kit (QIAGEN, Germany), and mixed with each sample at a ratio of 1:1 to be used as a template. Then, PCR was performed thereon again by using NV ORF primers in the same conditions as above. Following PCR, the resulting PCR products were subjected to electrophoresis, and then, DNA bands were observed using an UV detector. The amplified PCR products were recovered by using the gel purification kit (QIAGEN, Germany), and cloned by using the TOPcloner™ TAcoreKit (Enzynomics, Korea) to perform the sequence analysis thereof.

The DNA products obtained by PCR were identified by using an agarose gel, and DNA fragments were obtained as shown in FIG. 1.

The DNA fragments were subjected to the sequence analysis thereof, to thereby identify mutations in VHSV NV DNA.

After obtaining DNA sequence information, ORF sequences of the VHSV NV gene were translated, and amino acid sequences were obtained therefrom. The amino acid sequences were aligned to identify sequences modified by mutation. All the procedures above were performed by using a Bioedit program.

Consequently, among 13 VHSV sequences separated from 13 flatfish, mutations occurred commonly in four sites (39 C/T, 253 C/T, 291 G/A, and 336 G/A), wherein such four DNA mutations were confirmed as mutations that did not change amino acids.

Besides the four common mutations sites, six non-overlapping DNA mutation sites were identified as shown in Table 3. It was confirmed that, as shown in Table 3, mutations in the amino acids of NV protein (Nos. 8, 56, 81, 88, 117, and 119) were induced at the DNA mutation sites.

TABLE 3

| Sequence mutation site | Sequence | Amino acid mutation site | Tm | GC | SEQ ID NO: |
|---|---|---|---|---|---|
| point mutation 23 (G → A) | CGGCACACAACACAACCAGC 20 bp | NO. 8 (S → N) | 59.5° C. | 60.00% | 3 |
| point mutation 167 (C → T) | CTAGAGTCTTAGAGGATCTAAG GAC 25 bp | NO. 56 (S → L) | 58.9° C. | 44.00% | 4 |
| point mutation 241 (A → G) | GTCTCCTAGAGGGAGCTCATTA C 23 bp | NO. 81 (T → A) | 60.2° C. | 52.17% | 5 |
| point mutation 262 (G → A) | CTAAGGAATATCCCCTCCAGTC C 23 bp | NO. 88 (V → I) | 60.2° C. | 52.17% | 6 |
| point mutation 350 (G → A) | GACGAATGACTCCGAATCTCCC 22 bp | NO. 117 (G → D) | 60.0° C. | 54.55% | 7 |

TABLE 3-continued

| Sequence mutation site | Sequence | Amino acid mutation site | Tm | GC | SEQ ID NO: |
|---|---|---|---|---|---|
| point mutation 355 (G → A) | GACGAATGGCTCCAAATCTCCC 22 bp | NO. 119 (E → K) | 58.1° C. | 50.00% | 8 |

<Example 2> Confirmation of Pathogenicity of VHSV Amino Acid Mutants

1. Confirmation of Wild-Type VHSV NV Protein Mutant Effects in Flatfish Cells

First, in flatfish cells, the degree of production of ATP, which is regarded as cell energy, was analyzed to confirm high pathogenicity of VHSV.

To efficiently express wild-type VHSV NV proteins in cells, wild-type VHSV NV genes were cloned into a pcDNA3 vector to prepare a recombinant vector.

The prepared recombinant vector was used for transduction into HINAE cells that are embryo cells of flatfish (National Institute of Fisheries Science), to thereby express VHSV NV proteins. After 24 hours of the transduction, the production of ATP which is regarded as cell energy was measured by using the ATP Bioluminescene Assay Kit (Roch Company, Swiss) according to the manufacturer's instructions. Accordingly, changes in cell energy production upon the VHSV NV protein expression were confirmed.

Figures 4, 5:
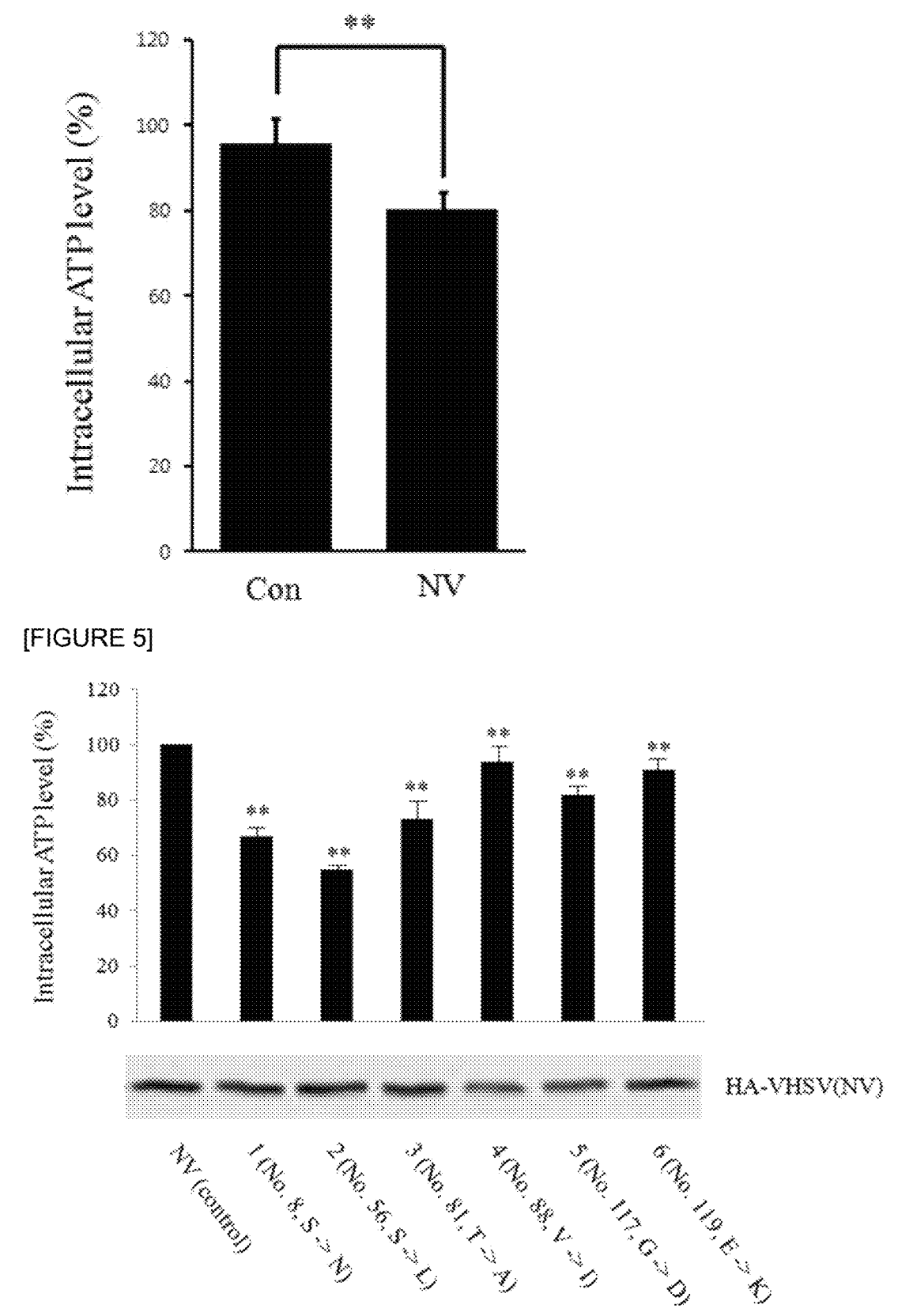

As a result, as shown in FIG. 4, it was confirmed that the VHSV NV protein expression caused a decrease in the production of ATP cell energy by about 20% in the flatfish cells.

2. Confirmation of Pathogenicity of Amino Acid Mutants of VHSV NV Protein

To confirm pathogenicity of six amino acid mutants of VHSV NV proteins, the sequences at the six amino acid mutation sites shown in Table 3 were cloned into a pcDNA3 vector to prepare a recombinant vector.

In the same manner as in Example 2-1, the prepared vector was used for transduction into flatfish cells, and then, expression of each of the six amino acid mutants (Nos. 8, S→N; No. 56, S→L; No. 81, T→A; No. 88, V→I; No. 117, G→D, and No. 119, E→K) was induced, to thereby analyze the yields of ATP.

As a result, as shown in FIG. 5, it was confirmed that the ATP production was reduced by up to 45% as compared with wild-type VHSV NV proteins, and that the amino acid mutant at No. 56 (serine→leucine) showed the greatest decrease among the six amino acid mutants.

In addition, since the protein function is closely related to the protein structure, hydropathy index, which is one of the most important factors in protein structure determination and indicates hydrophilicity/hydrophobicity of the protein, was confirmed as being substituted for each of the mutated amino acids (see Kyte J, Doolittle RF (May 1983). "A simple method for displaying the hydropathic character of a protein". J. Mol. Biol. 157 (1): 105-32).

As a result, as shown in FIG. 6, changes in the hydropathy index of all the mutants were confirmed. In particular, in FIG. 6B, the mutant at No. 56 (serine→leucine) showed the greatest change in hydropathy index thereof from −0.8 (serine) to +3.8 (leucine). Such a result was consistent with the results of the previous ATP yield analysis. Accordingly, it was confirmed that, due to the mutation at No. 56 amino acid, a rapid change in a three-dimensional structure of the NV protein was induced.

Based on the results above, it was confirmed that, in consideration of the close relation between the protein function and the protein structure, the structural change of the NV protein upon the mutation at No. 56 amino acid can affect high pathogenicity of VHSV, and in this regard, the mutation at No. 56 amino acid (serine→leucine) can be used as an effective pathogenic marker for early diagnosis of induction of VHSV-related high pathogenicity/death in flatfish.

The embodiments of the present invention described above are not intended to limit the spirit of the present invention. The scope of the present invention should be construed according to the following claims, and the spirit within the scope of the claims should be construed as being included in the scope of the present invention.

The invention claimed is:

1. A method of providing information for diagnosis of pathogenic viral hemorrhagic septicemia virus (VHSV), the method comprising:

sequencing DNA sequences of NV gene of VHSV from a VHSV-infected subject to obtain DNA sequence information;

converting the DNA sequence information obtained from the sequencing into amino acid information; and detecting a mutated amino acid sequence consisting of an amino acid in which serine (S) at the $56^{th}$ position is substituted with leucine (L);

preparing a recombinant vector by cloning the DNA sequence of a VHSV NV protein having the mutated amino acid into a pcDNA3 vector;

transducing the recombinant vector into HINAE cells for inducing expression of the VHSV NV protein having the mutated amino acid, and measuring adenosine triphosphate (ATP); and obtaining a reference ATP from a cell expressing a wild-type VHSV NV protein; and determine the mutated amino acid as an indicator of pathogenicity if the ATP of the cell expressing the VHSV NV protein having the mutated amino acid is lower than the reference ATP.

2. The method of claim 1, wherein the subject is selected from the group consisting of rockfish, flatfish, snapper, convict grouper, gray mullet, sea bass, gizzard shad, turbot, swellfish, mackerel, spotty belly greenling, tuna, croaker, yellow tail, horse mackerel, carp, leather carp, Japanese eel, catfish, loach, and crucian.

* * * * *